United States Patent
Heß et al.

(10) Patent No.: US 12,115,259 B2
(45) Date of Patent: Oct. 15, 2024

(54) SPHERICAL BEADS FOR USE IN PRODUCING PHARMACEUTICALLY ACTIVE PELLETS

(71) Applicant: Chemische Fabrik Budenheim KG, Budenheim (DE)

(72) Inventors: Tobias Heß, Niedernhausen (DE); André Huhn, Bischofsheim an der Rhön (DE); Christian Koch, Heidesheim (DE); Markos Papaioannou, Saulheim (DE); Daniel Zakowiecki, Budenheim (DE)

(73) Assignee: Chemische Fabrik Budenheim KG, Budenheim (DE)

( * ) Notice: Subject to any disclaimer, the term of this patent is extended or adjusted under 35 U.S.C. 154(b) by 197 days.

(21) Appl. No.: 17/281,442

(22) PCT Filed: Sep. 27, 2019

(86) PCT No.: PCT/EP2019/076135
§ 371 (c)(1),
(2) Date: Mar. 30, 2021

(87) PCT Pub. No.: WO2020/069987
PCT Pub. Date: Apr. 9, 2020

(65) Prior Publication Data
US 2022/0000784 A1    Jan. 6, 2022

(30) Foreign Application Priority Data
Oct. 4, 2018    (EP) .................................... 18198640

(51) Int. Cl.
*A61K 9/16*    (2006.01)

(52) U.S. Cl.
CPC .......... *A61K 9/1676* (2013.01); *A61K 9/1611* (2013.01); *A61K 9/1682* (2013.01)

(58) Field of Classification Search
CPC .. A61K 9/1676; A61K 9/1611; A61K 9/1682; A61K 9/1623; A61K 9/1652; A61K 9/1658; A61K 9/50
USPC ....................................................... 424/490
See application file for complete search history.

(56) References Cited

U.S. PATENT DOCUMENTS

| | | | | |
|---|---|---|---|---|
| 2008/0102131 A1* | 5/2008 | Nagira | ...................... | A61P 9/10 424/94.1 |
| 2010/0260856 A1* | 10/2010 | Konishi | ............... | A61K 31/167 424/490 |
| 2015/0050353 A1* | 2/2015 | Piene | ................... | A61K 9/1623 424/682 |

FOREIGN PATENT DOCUMENTS

| | | |
|---|---|---|
| EP | 2 223 702 A1 | 9/2010 |
| EP | 2 496 261 A2 | 9/2012 |
| EP | 2 659 882 A1 | 11/2013 |
| WO | WO-2004/032901 A1 | 4/2004 |
| WO | WO-2008/014175 A2 | 1/2008 |
| WO | WO-2010/059506 A1 | 5/2010 |
| WO | WO-2011/056775 A2 | 5/2011 |

OTHER PUBLICATIONS

Bowen, P., "Particle Size Distribution Measurement from Millimeters to Nanometers and from Rods to Platelets," Journal of Dispersion Science and Technology, vol. 23, No. 5, 2002, pp. 631-662.

* cited by examiner

*Primary Examiner* — Frederick F Krass
*Assistant Examiner* — Lucy M Tien
(74) *Attorney, Agent, or Firm* — Faegre Drinker Biddle & Reath LLP

(57) ABSTRACT

Improved spherical beads that may be used in producing pharmaceutically active pellets by depositing a pharmaceutically active agent on the surface of said spherical beads. The spherical beads includes a pharmaceutically acceptable carrier material, including:
   a) at least 60 wt. % of phosphoric acid calcium salt and
   b) up to 40 wt. % of organic material.
Greater than or equal to 90 wt % of the spherical beads have a particle size in the range of from 90 μm to 1200 μm. The spherical beads have:
   a bulk density of at least or more than 1000 g/l,
   a specific surface area of at most or less than 10 m²/g, and
   a hardness of at least or more than 600 g/mm². Also included is a method for producing such spherical beads and to pharmaceutically active pellets being prepared by depositing a pharmaceutically active agent on the surface of the spherical beads.

Figure 1:
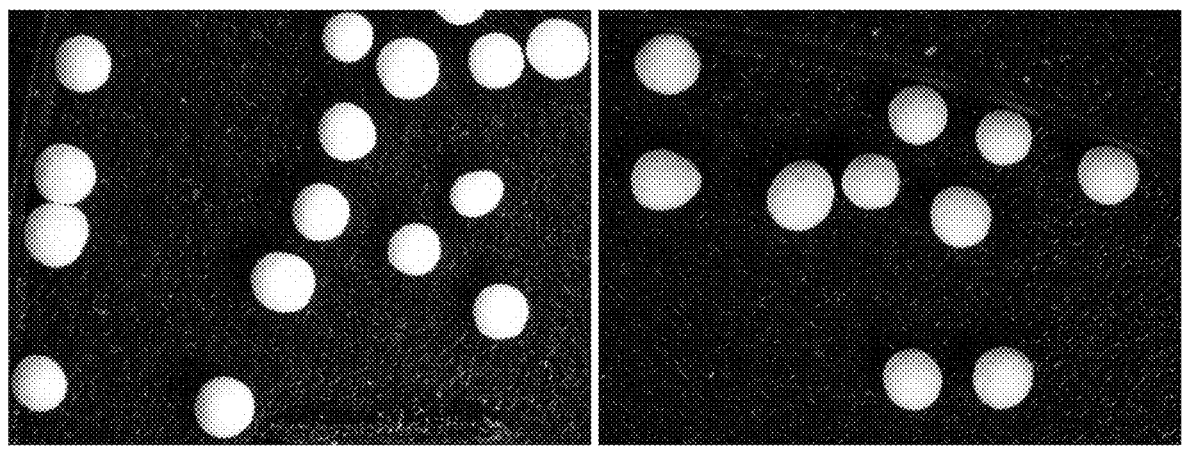

12 Claims, 2 Drawing Sheets

SPHERICAL BEADS FOR USE IN PRODUCING PHARMACEUTICALLY ACTIVE PELLETS

CROSS REFERENCE TO RELATED APPLICATIONS

This application is a National Stage of International Application No. PCT/EP2019/076135 filed Sep. 27, 2019, which claims benefit of European Patent Application No. 18 198 640.7 filed Oct. 4, 2018, both of which are herein incorporated by reference in their entirety.

The present invention is directed to spherical beads for use in producing pharmaceutically active pellets being prepared by depositing a pharmaceutically active agent on the surface of said spherical beads, wherein the spherical beads consist of a pharmaceutically acceptable carrier material. Further, the invention is directed to a method for producing such spherical beads and to pharmaceutically active pellets being prepared by depositing a pharmaceutically active agent on the surface of the spherical beads.

An increasing number of medicinal products are being marketed as multi-unit dosage forms. Multi-unit dosage forms are considered to be advantageous over single-unit dosage forms thanks to improved effectiveness and safety. These forms have been gaining popularity in recent years because of several reasons including the possibility of preparation of modified release formulations, physical separation of incompatible substances as well as overcoming the swallowing difficulties, especially in pediatric and elderly patients.

Multi-unit dosage forms are frequently produced by the layering technique which consists in applying layers of a pharmaceutically active material (e.g. a drug solution, a drug suspension or a drug powder) onto spherical beads (pellets) with dimensions lower than 1.5 mm. The spherical beads used consist of pharmaceutically acceptable compounds, such as microcrystalline cellulose (MCC), lactose, starch, sugars, silicon dioxide, carnauba wax.

EP 2 223 702 A1 discloses core particles for pharmaceutical preparations comprising a pharmaceutically acceptable inorganic material selected from calcium hydrogen phosphate, silicon dioxide, aluminum hydroxide and aluminum silicate. According to the examples the core particles are produced by wet granulation and contain 100% of an inorganic material selected from the above mentioned materials. In the wet granulation process disclosed 20% of ethanol are used in order to improve the mechanical strength of the product. Accordingly, some of the ethanol used in the process can remain in the final product, which is undesirable in some specific applications.

EP 2 659 882 A1 discloses disintegrating particles. However, coating of disintegrating pellets with aqueous suspensions or solutions can prove to be challenging as even small amount of liquid can start disintegration process at least at the surface of the pellets.

EP 2 496 261 discloses co-processed excipient made of a mixture of microcrystalline cellulose and calcium phosphate. The components are mixed in a weight ratio of from about 85:15 to about 55:45 microcrystalline cellulose:calcium phosphate. The co-processed product is intended to be used in processes involving multiple compaction steps. However, microcrystalline cellulose contains quite high amount of water, which can be problematic in case of water-sensitive pharmaceutically active agents. Moreover, microcrystalline cellulose starts to swell upon contact with water. Therefore, in some applications the presence of large amounts of microcrystalline cellulose in pellets is undesirable.

It is an object of the present invention to solve the above mentioned problems in the art by providing improved spherical beads that may be used in producing pharmaceutically active pellets by depositing a pharmaceutically active agent on the surface of said spherical beads.

This object is achieved by providing spherical beads consisting of a pharmaceutically acceptable carrier material, said carrier material consisting of
  a) at least 60 wt. % of phosphoric acid calcium salt and
  b) up to 40 wt. % of organic material,
wherein ≥90 wt % of the spherical beads have a particle size in the range of from 90 μm to 1200 μm, and wherein the spherical beads have
  a bulk density of at least 1000 g/l,
  a specific surface area of at most 10 $m^2/g$ and
  a hardness of at least 600 $g/mm^2$.

The spherical beads of the present invention are characterized by an elevated density, favorable spherical shape and sufficient mechanical strength as well as excellent chemical and physical stability. Moreover they have a very smooth and dense surface with minimum porosity. The calcium phosphate-based spherical beads of the present invention are generally insoluble in water. They have very good mechanical strength and their properties do not change even during long contact with water.

Even when stirred with water for 24 hours the pellets do not swell or disintegrate, do not change their size or shape significantly. Additionally moisture uptake, even under conditions of a high relative humidity (above 90% RH) is limited and does not exceed 3.5-4% w/w. Such properties make the spherical beads of the present invention ideal candidates for further coating, especially with water solutions or suspension without the risk of any damage to the surface of the beads or any negative effect on the properties of multiparticulate dosage forms being prepared from the inventive spherical beads.

The inventive spherical beads consist of a pharmaceutically acceptable carrier material, wherein the term "pharmaceutically acceptable material" as used herein, refers to materials that are generally regarded as safe (GRAS classification of the American Food and Drug Administration, USFDA) for use in pharmaceutical products, particularly when the compositions are to be administered by the oral route.

Any organic carrier material present in the beads is dispersed in the calcium phosphate matrix. This effectively suppresses or at least minimizes any unwanted interactions of organic carrier material with pharmaceutically active agents.

Moreover, due to the specific constitution of the inventive beads their moisture content is very low and they do not tend to water uptake. Therefore, the calcium phosphate-based spherical beads of the invention are suitable for processing water-sensitive active agents. In some embodiments of the invention the moisture content is less than 2 wt. % or even less than 1 wt. %, wherein the moisture content of the inventive spherical beads is expressed as loss on drying and is determined by thermogravimetric analysis, wherein the spherical beads are dried using a sensitive electrobalance under the temperature of 105° C. to constant mass. The moisture content is defined as the percentage loss in weight of the sample.

According to the present invention the spherical beads comprise at least or more than 60 wt. % of phosphoric acid calcium salt. In specific embodiments of the invention the carrier material comprises at least or more than 70 wt. %, of at least or more than 80 wt. % or of at least or more than 90 wt. % of phosphoric acid calcium salt. In some embodiments of the invention the maximum amount of phosphoric acid calcium salt in the carrier material is 79 wt. %, 89 wt. % or even 99 wt. %. In some specific embodiments the inventive spherical beads consist of 100 wt. % phosphoric acid calcium salt component.

The calcium phosphate-based spherical beads of the invention are insoluble in water. Further, the inventive spherical beads do not disintegrate upon contact with water. Therefore, coating process with the use of aqueous solutions or suspensions can be carried out with high spray rates without impacting the beads' surface and their further performance.

In specific embodiments of the invention the phosphoric acid calcium salt is selected from the group consisting of monobasic calcium phosphate, dibasic calcium phosphate, tribasic calcium phosphate and mixtures thereof. In some embodiments the phosphoric acid calcium salt is anhydrous or contains water of hydration. Accordingly, the phosphoric acid calcium salt used can be anhydrous, a hydrate or mixtures thereof.

According to the present invention the spherical beads comprise up to or less than 40 wt. % of organic material. In specific embodiments of the invention the carrier material comprises up to or less than 30 wt. %, up to or less than 20 wt. % or up to or less than 10 wt. % of organic material. In some embodiments of the invention the minimum amount of organic material in the carrier material is 21 wt. %, 11 wt. % or 1 wt. %.

In specific embodiments of the invention the organic material is selected from the group consisting of microcrystalline cellulose, lactose, gelatin, cellulose and its derivatives, starch and its derivatives, saccharides and polysaccharides, sugar alcohols (e.g. mannitol, sorbitol), synthetic polymers and mixtures thereof. In some embodiments the organic material is anhydrous or contains water of hydration. Accordingly, the organic material used can be anhydrous, a hydrate or mixtures thereof.

The inventive spherical beads consist of a pharmaceutically acceptable carrier material as indicated above, i.e. they do not comprise any other solid component except for the phosphoric acid calcium salt component indicated above and the organic material component indicated above. For instance, in those embodiments, where the inventive spherical beads comprise 60 wt. % of phosphoric acid calcium salt they comprise 40 wt. % of the organic material referring to the solid content of the spherical beads. Accordingly, in those embodiments, where 100 wt. % of the inventive spherical beads consist of the phosphoric acid calcium salt component, there is no organic material in the carrier material at all.

According to the present invention ≥90 wt. % of the spherical beads have a particle size in the range of from 90 μm to 1200 μm. In specific embodiments of the invention the particle size is in the range of from 100 μm to 1100 μm or in the range of from 100 μm to 1000 μm. The particle size of the inventive spherical beads is determined by analytical sieving as indicated in European Pharmacopoeia (Ph. Eur.), 9th Edition. As the spherical beads according to the present invention are free-flowing and are larger than 75 μm mechanical agitation is applied.

According to the present invention the spherical beads have a bulk density of at least or more than 1000 g/l. In specific embodiments of the invention the spherical beads have a bulk density of at least or more than 1100 g/l, at least or more than 1200 g/l or even at least or more than 1250 g/l. The bulk density of the inventive spherical beads is determined in a dry graduated 250 ml cylinder according to the procedures as indicated in European Pharmacopoeia (Ph. Eur.), 9th Edition.

Due to the inventive spherical beads having a high density, this allows producing very heavy drug products with prolonged residence time in the stomach. Prolonged gastric residence time is curtail for many pharmaceutically active agents which are locally active in the stomach or have a narrow absorption window in the stomach or in the upper small intestine.

According to the present invention the spherical beads have a specific surface area of at most or less than 10 $m^2/g$. In specific embodiments of the invention the specific surface area is at most or less than 9 $m^2/g$, 8 $m^2/g$ or 7 $m^2/g$. The specific surface area of the spherical beads is determined by calculating the amount of gas adsorbed on the surface of the beads according to the procedures as indicated in European Pharmacopoeia (Ph. Eur.), 9th Edition.

The low specific surface area of the inventive beads is an indicator for the beads having a very dense and smooth surface. Accordingly, the risk of solutions or suspensions of pharmaceutically active agent to be deposited on the surface of the spherical beads flowing or penetrating into pores on the bead surface is very low. This is important for controlling the amount of pharmaceutically active agent deposited on the surface of the beads as well as its homogenous distribution on the surface, which has an influence on release time and bioavailability of the agent.

According to the present invention the spherical beads have a hardness of at least or more than 600 $g/mm^2$. In specific embodiments of the invention the spherical beads have a hardness of at least or more than 700 $g/mm^2$ or even a hardness of at least or more than 800 $g/mm^2$. The Hardness of the spherical beads is determined by a texture analyzer by compressing a spherical bead and measuring the maximum force reached prior to a fracture of a particle (F). Then the hardness is calculated using the equation: $F/\pi R^2$ where R is the maximum radius of the spherical bead.

According to the present invention the spherical beads have a sphericity of at least or more than 0.80. In specific embodiments of the invention the spherical beads have a sphericity of at least or more than 0.90 or even a sphericity of at least or more than 0.95. The sphericity (circularity) of the spherical beads is determined by an image analysis by measuring a degree of which the particle is similar to a perfect circle. Sphericity (circularity) is calculated from the equation: $4\pi A/P2$ where A is the particle area and P is its perimeter. Particle area and its perimeter are measured with the help of suitable optical microscope equipped with software allowing image analysis.

The high degree of sphericity of the inventive beads allows better homogenous distribution of pharmaceutically active agents on the bead surface. In cases where the pharmaceutically active agent is deposited on the bead surface in the form of a layer a more even layer thickness can be achieved over the entire bead surface.

According to the present invention the spherical beads have a surface roughness of at least or more than 0.90. In specific embodiments of the invention the spherical beads have a surface roughness of at least or more than 0.92 or even a surface roughness of at least or more than 0.95. The surface roughness is determined by measurement of particle edge roughness (convexity) and is calculated by dividing the convex hull perimeter by the actual particle perimeter using the equation: Pc/P where Pc is defined as the convex hull perimeter and P the actual perimeter. P and Pc are measured with the help of suitable optical microscope equipped with software allowing image analysis.

The low surface roughness of the inventive beads allows better homogenous distribution of pharmaceutically active agents on the bead surface. In cases where the pharmaceutically active agent is deposited on the bead surface in the form of a layer a more even layer thickness can be achieved over the entire bead surface.

The inventive spherical beads are characterized in that they do not disintegrate when being placed in water at a temperature of 25±1° C. and being kept there for 24 h. Particularly, the spherical beads according to the invention are characterized in that after having been placed in water at a temperature of 25±1° C. and being kept there for 24 h while being stirred with a speed of 50 rpm≥90 wt. % of the spherical beads still have essentially the same particle size as before. Particularly, the circle equivalent diameter of the beads reduces by less than 1%. The circle equivalent (CE) diameter is the diameter of a circle with the same area as the particle: CE diameter=$(4A/\pi)^{1/2}$, where A is a particle projected area. The particle projected area is measured with the help of a suitable optical microscope equipped with software allowing image analysis.

Furthermore, the surface roughness remains essentially the same. Particularly, the value of surface roughness of the beads reduces by less than 1%.

The present invention is also directed to a method for producing spherical beads for use in producing pharmaceutically active pellets being prepared by depositing a pharmaceutically active agent on the surface of said spherical beads, wherein the spherical beads consist of a pharmaceutically acceptable carrier material, wherein the carrier material consists of
   a) at least 60 wt. % of phosphoric acid calcium salt and
   b) up to 40 wt. % of organic material,
   and wherein the spherical beads are obtained by mixing the carrier material and water in a mixing device for at least 1 minute and up to 10 minutes, thereby producing a mixture, wherein the temperature of said mixture is increased by 4 to 6° C. per minute by means of the mechanical mixing energy applied by the mixing device to the mixture, only.

Increasing the temperature of mixture by means of the mechanical mixing energy applied by the mixing device to the mixture, only, means that there is no external heat input to the mixture by means of e.g. an external heating source being located outside the mixing vessel. Further, there is no heating through the mixing vessel wall. Besides the mixture is not preheated before being feed into the mixing vessel.

Pharmaceutically acceptable starting carrier materials used as the carrier material in the inventive method are commonly available on the market. They do not require any specially treatment or processing before mixing the carrier material and water in the mixing device.

In a specific embodiment of the invention, starting carrier materials having an average particle size of higher than 20 µm (volume-based distribution) as measured by laser diffraction method are used. This results in producing beads of high diameters and unexpectedly high mechanical strength.

In the inventive manufacturing process neither organic solvents nor catalysts are used. So, there are neither residual solvents nor residual catalysts in the finished spherical beads of the invention that can have a detrimental effect on the stability of the pharmaceutically active agent.

The inventive spherical beads are obtainable by means of said method. Accordingly, in a specific embodiment of said method there are produced spherical beads of the aforementioned kind, characterized in that ≥90 wt. % of the spherical beads have a particle size in the range of from 90 µm to 1200 µm, and wherein the spherical beads obtained by said method have
   a bulk density of at least 1000 g/l,
   a specific surface area of at most 10 $m^2/g$ and
   a hardness of at least 600 $g/mm^2$.

The mixing device used for production of spherical beads according to this invention allows high-speed mixing leading to direct micro-pelletizing. The high-speed mixing action is implemented through a mixing tool, wherein said mixing tool has one or more mixing blades. In specific embodiments of the invention the rotational speed of the outermost part of the mixing blade is higher than 15 m/s, higher than 20 m/s or even higher than 25 m/s.

In specific embodiments the mixing tool is arranged eccentrically in a rotating mixing pan, wherein the mixing pan rotates in the opposite direction as compared to the direction of rotation of the mixing tool, wherein the rotational speed is at least 30 rpm, at least 40 rpm or at least 45 rpm. In specific embodiments of the invention the mixing pan is arranged at an angle in the range of from 15 to 45°.

As compared to the common wet granulation process the high-energy mixing process according to the present invention releases far more energy by heat. This can be observed by fast increase of temperature of the mixture during the process. During high-speed mixing increase in temperature of the mixture reaches 4-6° C./min. Depending on how long the mixing process is performed this may result in the mixture reaching temperatures of more than 30° C., more than 40° C., more than 50° C. or even more than 60° C. In specific embodiments of the invention the maximum temperature reached in the mixing process is less than 70° C., less than 60° C., less than 50° C. or even less than 40° C.

Forces involved in the high-speed mixing process of the invention causes not only rapid temperature increase but also strong compression of powders which apparently results in higher density and lower porosity of the spherical beads obtained.

When perform the commonly used wet granulation equipment such as high shear granulator or fluid bed granulator the energy involved in the process is not sufficient to densify a powder mass adequately and create durable bonds between particles. Observed increase in the process temperature is usually in the range of from 5 to 6° C. in total, but does not exceed 10° C. except the mixture is actively heated by means of an external heating device. The common wet granulation process produces granules of irregular shape and relatively high porosity. Such granules are agglomerates of insufficient mechanical strength and very broad particle size distribution, from very fine particles to big lumps.

Surprisingly it was found that the combination of the specific mixing process of the invention and the specific inventive mixture of phosphoric acid calcium salt and organic component (e.g. microcrystalline cellulose) allows direct preparation of spherical beads of favorable physical characteristic. Moreover it allows using commonly available standard raw materials which do not require any specially treatment or processing adjusting their functional properties prior further processing.

Additionally it was found that in this specific process the application of particles of higher average size, exceeding 20 um, allows controlling of the size of spherical beads.

The inventive method is simple and very fast, and the beads obtained by the process are spherical enough and can be directly dried, wherein the drying step can performed in different types of dryers including try dryer, fluid bed dryer, rotary kiln etc. However it was observed that the fastest and the most reliable is fluid bed drying process. The temperature of drying should be sufficient to remove the water from the beads. In specific embodiments the drying temperature is above 60° C., more preferably above 70° C. and the most preferably above 80° C. The content of moisture in the final spherical beads depends on amount of organic component and preferably is lower than 2% w/w, and more preferably lower that 1% w/w.

Optionally, in order to further improve the degree of sphericity of the beads a short spheronization step can be performed before drying. However, usually spheronization is not required in order to obtain the desired physical characteristics of the inventive spherical beads. Accordingly, in some embodiments of the invention the inventive spherical beads having the physical characteristics as indicated above are obtainable without any spheronization step.

The inventive spherical beads are suitable for producing pharmaceutically active pellets being prepared by depositing a pharmaceutically active agent on the surface of said spherical beads. In specific embodiments of the invention the pharmaceutically active agent is deposited on the surface of the spherical beads by means of depositing a solution, a suspension or a powder of said pharmaceutically active agent on the surface of the spherical beads. In even further specific embodiments the solution, the suspension or the powder of the pharmaceutically active agent forms a layer on the surface of the spherical beads.

In light of the above any pharmaceutically active pellets in accordance with the present invention consist of the inventive spherical beads having deposited on their surface a pharmaceutically active agent. As said pellets are mainly composed of the inventive spherical beads they do substantially have the same physical characteristics, such as spherical shape, bulk density, specific surface area, hardness, degree of sphericity, surface roughness, etc., as the inventive spherical beads alone, i.e. without any pharmaceutically active agent deposited on their surface.

As used herein, the term "pharmaceutically active agent" refers to any agent, drug, compound, composition or mixture, which provides some pharmacologic effect that can be demonstrated in-vivo or in vitro. A substance exhibiting a "pharmacologic effect" is capable of interacting with any type of cells present in or on the body of a human or animal, including both, the body's own cells or other cells, such as bacteria, viruses or parasites. Due to its pharmacologic effect a pharmaceutically active agent is capable of reconstituting, rectifying or positively influencing a physiological function of the body in order to prevent, shorten, partially or completely remedy a disorder, or to alleviate or eliminate the symptoms of the disorder.

The following examples show some of the features of specific embodiments of the present invention. However, the skilled reader will understand that those embodiments are just exemplary but do not restrict the inventive idea to exactly the combination of features of the embodiments of the examples.

In the examples mentioned below it is referred to FIGS. 1 and 2, wherein

Figure 2:
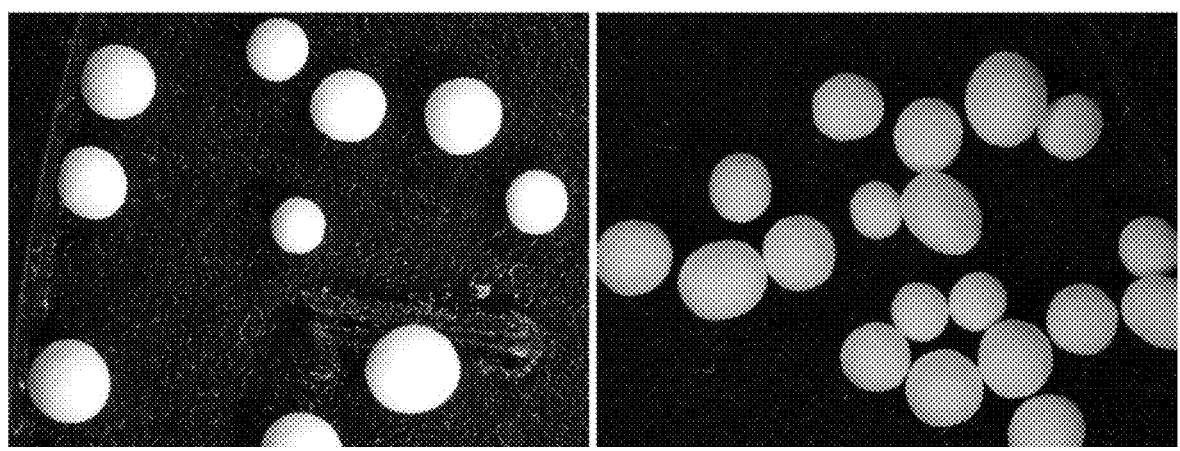
Figure 3:
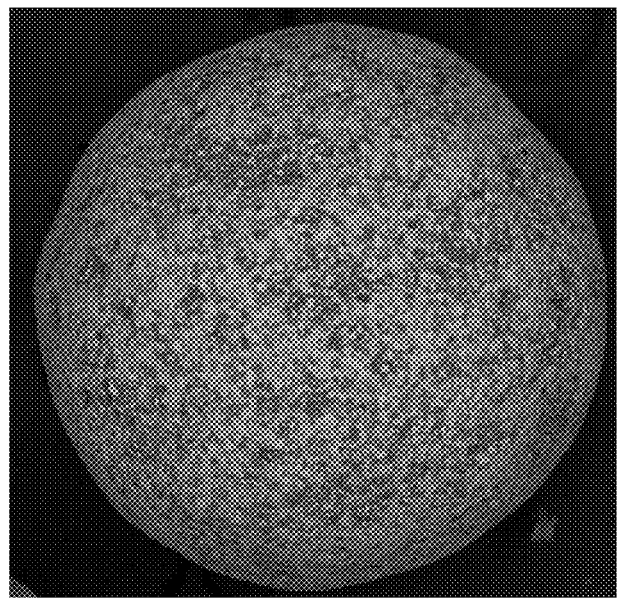
Figure 3:
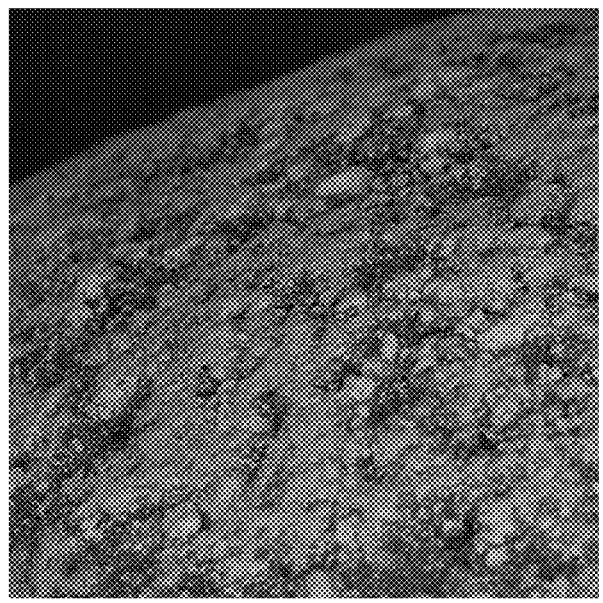

FIG. 1 shows a microscopic photograph of inventive spherical beads containing 80% of dibasic calcium phosphate anhydrous (Example 1) before (left) and after (right) 24 hours mixing with water, FIG. 2 shows a microscopic photograph of inventive spherical beads containing 60% of dibasic calcium phosphate anhydrous (Example 2) before (left) and after (right) 24 hours mixing with water, and wherein FIG. 3 shows SEM micrographs of a spherical bead prepared according to Example 1 as well as a close-up of the bead surface.

EXAMPLES

Examples 1-4

Preparation of Calcium Phosphate-Based Spherical Beads

Calcium salt of orthophosphoric acid was placed in a mixing pan of a high-energy mixing device (Eirich, Intensive mixer type RV01) together with an organic component. The grade of each component and the ratio between the two components is presented in the Table 1.

After addition of water the powder mass was blended for 1 minute. The mixing pan was rotated clockwise with the speed of 45 rpm. The mixing tool was rotated counterclockwise with the speed of 27 m/s. The amount of water used depends on the ration between components and is given in Table 1 expressed as percentage in relation to the mass of dry components. The wet material obtained from the high-energy mixing process was then transferred to a spheronizer and spheronized for 10 minutes with a speed of 800 rpm. The obtained spherical beads were dried in a fluid-bed drier at a temperature of 80° C. for around 30 minutes—until value of LoD determined at a moisture analyzer balance at 105° C. was below 1-2%. The dry spherical beads were then classified between sieves of 100 μm and 1000 μm and analyzed further. Table 2 shows the physical characteristics of the obtained beads.

TABLE 1

| | Median particle size* [μm] | Example 1 | Example 2 | Example 3 | Example 4 |
|---|---|---|---|---|---|
| Dibasic calcium phosphate anhydrous | 25 | 80% | — | 80% | 60% |
| Dibasic calcium phosphate anhydrous | 60 | — | 80% | — | — |
| Microcrystalline cellulose type 101 | 65 | 20% | 20% | — | 40% |
| Microcrystalline cellulose type 105 | 15 | — | — | 20% | — |
| Water | | 35% | 35% | 35% | 45% |

*starting material

TABLE 2

| Parameter | Example 1 | Example 2 | Example 3 | Example 4 |
|---|---|---|---|---|
| Bulk density | >1100 g/l | >1100 g/l | >1100 g/l | >1000 g/l |
| Degree of sphericity | ≥0.9 | ≥0.9 | ≥0.9 | ≥0.9 |
| LoD | <1% | <1% | <1% | <2% |
| Friability | <1% | <1% | <1% | <1% |
| Hardness | >600 g/mm$^2$ | >600 g/mm$^2$ | >600 g/mm$^2$ | >600 g/mm$^2$ |
| Angle of repose | <30° | <30° | <30° | <30° |

FIG. 3 shows SEM micrographs of a spherical bead prepared according to Example 1 as well as a close-up of the bead surface. The micrographs reveal very dense and porous-free surface of these beads which indicate very small specific surface area. Moreover, one can distinguish the lighter spots of calcium phosphate and darker of microcrystalline cellulose uniformly distributed in the bead.

Example 5

Physical Stability of Beads in Contact with Water

Beads prepared according to Example 1 and 4 containing 80% w/w and 60% w/w respectively were placed in water at a temperature of 25±1° C. for 24 h. During this time the liquid was stirred with a speed of 50 rpm. Before and after experiment they were tested in terms of bulk density, particle size and surface roughness. The results are given in the Table 3 and represented by FIGS. 1 and 2.

The results show essentially no changes in bead properties after 24 hours mixing with water. One can notice an insignificant decrease in bead size caused by the partial dissolution of the substance from the surface and erosion during such a long mixing time. Nevertheless this phenomenon did not impact significantly on the particles surface or shape.

TABLE 3

| Parameter | Beads containing 80% of dibasic calcium phosphate anhydrous | | Beads containing 60% of dibasic calcium phosphate anhydrous | |
|---|---|---|---|---|
| | initial | mixed with water for 24 h | initial | mixed with water for 24 h |
| Bulk density | >1100 g/l | >1100 g/l | >1000 g/l | >1000 g/l |
| Circle Equivalent diameter | 752 ± 63 μm | 749 ± 59 μm | 923 ± 138 μm | 917 ± 104 μm |
| Maximum diameter | 786 ± 78 μm | 784 ± 75 μm | 984 ± 204 μm | 969 ± 118 μm |
| Minimum diameter | 724 ± 57 μm | 716 ± 48 μm | 878 ± 119 μm | 876 ± 95 μm |
| Surface roughness | 0.996 ± 0.005 | 0.995 ± 0.007 | 0.982 ± 0.033 | 0.980 ± 0.021 |

Example 6

Effect of Spheronization

The physical properties of beads produced with or without additional spheronization step have been analyzed. Particularly, beads prepared according to Example 1 have been used in this respect, and the results of this experiment are indicated in the below table 4.

The data show that spheronization is not required in order to obtain the physical characteristics of the inventive spherical beads. Accordingly, the inventive spherical beads having the physical characteristics as claimed are obtainable without any spheronization step.

TABLE 4

| Parameter | beads before spheronization | beads after spheronization |
|---|---|---|
| Bulk density | 1000-1100 g/l | 1100-1200 g/l |
| Degree of sphericity | 0.87 ± 0.03 | 0.93 ± 0.01 |
| Surface roughness | 0.97 ± 0.02 | 0.99 ± 0.01 |

The invention claimed is:

1. Spherical beads for use in producing pharmaceutically active pellets prepared by depositing a pharmaceutically active agent on the surface of said spherical beads, wherein the spherical beads consist of a pharmaceutically acceptable carrier material, said carrier material consisting of a mixture of:
  a) at least 60 wt. % of a phosphoric acid calcium salt, wherein the phosphoric acid calcium salt is dibasic calcium phosphate; and
  b) at least 20 wt. % and up to 40 wt. % of an organic material, wherein the organic material is selected from the group consisting of microcrystalline cellulose, cellulose and its derivatives and mixtures thereof,
  wherein ≥90 wt. % of the spherical beads have a particle size in the range of from 90 μm to 1200 μm, and wherein the spherical beads have:
    a bulk density of at least 1000 g/l,
    a specific surface area of at most 10 m$^2$/g, and
    a hardness of at least 600 g/mm$^2$, and
  wherein the spherical beads do not disintegrate when placed in water at a temperature of 25±1° C. for 24 hours.

2. The spherical beads according to claim 1, wherein the phosphoric acid calcium salt is anhydrous or contains water of hydration.

3. The spherical beads according to claim 1, wherein the spherical beads have a sphericity of at least 0.8.

4. The spherical beads according to claim 1, wherein the spherical beads have a surface roughness of at least 0.9.

5. The spherical beads according to claim 1, wherein the circle equivalent diameter of the beads reduces by less than 1% when placing the beads in water at a temperature of 25±1° C. for 24 hours and stirring with a speed of 50 rpm.

6. Pharmaceutically active pellets prepared by depositing a pharmaceutically active agent on the surface of the spherical beads according to claim 1.

7. The pharmaceutically active pellets according to claim 6, wherein the pharmaceutically active agent is deposited on the surface of the spherical beads by depositing a solution, a suspension or a powder of said pharmaceutically active agent on the surface of the spherical beads.

8. The pharmaceutically active pellets according to claim 7, wherein the solution, the suspension or the powder of the pharmaceutically active agent forms a layer on the surface of the spherical beads.

9. A method for producing spherical beads for use in producing pharmaceutically active pellets being prepared by depositing a pharmaceutically active agent on the surface of said spherical beads, wherein the spherical beads consist of a pharmaceutically acceptable carrier material, wherein the carrier material consists of a mixture of:
  a) at least 60 wt. % of a phosphoric acid calcium salt, wherein the phosphoric acid calcium salt is dibasic calcium phosphate; and
  b) at least 20 wt. % and up to 40 wt. % of an organic material, wherein the organic material is selected from the group consisting of microcrystalline cellulose, cellulose and its derivatives, and mixtures thereof, and wherein the spherical beads are obtained by mixing the carrier material and water in a mixing device for at least 1 minute and up to 10 minutes, thereby producing a mixture, wherein the temperature of said mixture is increased by 4 to 6° C. per minute by the mechanical mixing energy applied by the mixing device to the mixture, only,
  wherein ≥90 wt. % of the spherical beads have a particle size in the range of from 90 μm to 1200 μm, and wherein the spherical beads have:
    a bulk density of at least 1000 g/l,
    a specific surface area of at most 10 m$^2$/g, and
    a hardness of at least 600 g/mm$^2$, and
  wherein the spherical beads do not disintegrate when placed in water at a temperature of 25 #1° C. for 24 hours.

10. Spherical beads for use in producing pharmaceutically active pellets prepared by depositing a pharmaceutically active agent on the surface of said spherical beads, wherein the spherical beads consist of a pharmaceutically acceptable carrier material, said carrier material consisting of a mixture of:
  a) at least 60 wt. % of a phosphoric acid calcium salt; and
  b) at least 20 wt. % and up to 40 wt. % of an organic material,
  wherein ≥90 wt. % of the spherical beads have a particle size in the range of from 90 μm to 1200 μm, and wherein the spherical beads have:
    a bulk density of at least 1000 g/l,
    a specific surface area of at most 10 m$^2$/g, and
    a hardness of at least 600 g/mm$^2$,
  wherein the spherical beads do not disintegrate when being placed in water at a temperature of 25±1° C. for 24 hours.

11. The spherical beads according to claim 10, wherein the organic material is selected from the group consisting of microcrystalline cellulose, lactose, gelatin, cellulose and its derivatives, starch and its derivatives, saccharides and polysaccharides, synthetic polymers and mixtures thereof.

12. The spherical beads according to claim 11, wherein the organic material is anhydrous or contains water of hydration.

* * * * *